United States Patent [19]

Dingwall et al.

[11] Patent Number: 5,003,983
[45] Date of Patent: Apr. 2, 1991

[54] CARDIAC MONITORING SYSTEM

[75] Inventors: Robert P. Dingwall, Clinton Corners; Howard T. Bellin, New York, both of N.Y.

[73] Assignee: Cortec, Inc., New York, N.Y.

[21] Appl. No.: 236,899

[22] Filed: Aug. 25, 1988

[51] Int. Cl.$^5$ ............................................. A61B 5/04
[52] U.S. Cl. .................................. 128/704; 128/702; 128/696
[58] Field of Search ............... 128/704, 703, 702, 696

[56] References Cited

U.S. PATENT DOCUMENTS

| | | | |
|---|---|---|---|
| 3,267,934 | 8/1966 | Thornton | 128/704 |
| 3,554,187 | 1/1971 | Glassner et al. | 128/703 |
| 3,822,696 | 7/1974 | Ekstrom et al. | 128/703 |
| 3,858,034 | 12/1974 | Anderson | 128/704 |
| 3,868,567 | 2/1975 | Ekstrom | 128/704 |
| 3,927,663 | 12/1975 | Russell et al. | 128/702 |
| 4,172,459 | 10/1979 | Hepp | 128/697 |
| 4,473,078 | 9/1984 | Angel | 128/419 D |
| 4,546,776 | 10/1985 | Bellin et al. | 128/704 |
| 4,754,762 | 7/1988 | Stuchl | 128/704 |

FOREIGN PATENT DOCUMENTS 3633983  4/1988  Fed. Rep. of Germany ...... 128/696

OTHER PUBLICATIONS

Taylor et al., "Digital Filtering of the ECG," Medical and Biological Engineering, 7-1974, pp. 493-502.

Primary Examiner—Lee S. Cohen
Assistant Examiner—Kennedy J. Schaetzle
Attorney, Agent, or Firm—Hopgood, Calimafde, Kalil, Blaustein, Judlowe

[57] ABSTRACT

A cardiac monitor system reads an EKG signal and conditions the EKG waveform in a manner that accentuates the information on ST segment location, within the waveform. ST segment location is used to modulate pulse width of a generated square wave permitting fast and accurate access to information regarding ST segment elevation and depression.

12 Claims, 5 Drawing Sheets

ST SEGMENT
NORMAL

ST SEGMENT
DEPRESSION

ST SEGMENT
ELEVATION

CARDIAC MONITORING SYSTEM

The present invention generally relates to a cardiac monitoring system, and more specifically, to a system, and device capable of measuring heart rate and the deviation in the ST segment of an electrocardiogram, and providing an output, including alarms, corresponding to the measured deviations in the ST segment.

In the course of the normal functioning of the heart muscle, a series of electrical discharges are produced in a periodic manner, forming a regular but complex waveform. This waveform is routinely monitored and recorded in the process of examining the operation of the heart. The monitored waveform is referred to as an electrocardiogram or "EKG".

The complex waveform of an EKG has been divided into characteristic segments to enhance understanding of the heart's operation. More particularly, the waveform associated with a single heartbeat is shown in FIG. 1. In this FIG., the peaks and valleys of the EKG waveform are labeled, by convention, and respectively designated as P, Q, R, S and T. Various portions of this waveform such as QRS complex, and the ST segment have special significance in examining the heart. For example, the ST segment, i.e., the portion of the EKG waveform between the S and T points in FIG. 1, has been found to correspond to certain pathologies of heart functioning. Often, the depression of the ST segment from its normal position indicates subendocardial ischemia, i.e., a lack of blood flow to that section of the heart muscle. In addition, ST segment elevation will often indicate localized blood flow problems such as the inferior or anteroseptal eschemia. In this context, ST segment elevation or depression is the change in the ST segment location relative to a normal value. As can be seen in FIG. 1, the normal ST segment value is located close to the isoelectric line of the EKG. The elevated ST segment is above the isoelectric line, while a depressed ST segment is below the isoelectric line. Overall, ST segment deviation, either depressed or elevated, provides a significant indicator of myocardial ischemia and, as such, is a powerful tool in detecting and predicting heart malfunctions.

Although the importance of the ST segment and associated deviations is now generally recognized, its precise measurement has remained difficult. This is especially true when the measurement is desired during an exercise period or some other independent activity by a patient. In the past, efforts to monitor the ST segment and its changes from a normal value have involved either direct monitoring of the EKG readout, via oscilloscope, or the use of complex software for bit-by-bit mapping of the ST segment over an extended interval. These approaches have not satisfied the need for a quick, accurate and unobtrusive means for monitoring deviations of the ST segment.

It is, therefore, an object of the present invention to provide an improved cardiac monitoring system.

It is an additional object of the present system to provide a monitor capable of measuring deviations in the ST segment of an EKG waveform.

It is another object of the present invention to provide a device to measure the deviation of the ST segment from the normal value in an EKG waveform, measure the pulse rate, and provide an output of the ST deviation and pulse rate, including an alarm corresponding to set excursions of ST deviation and pulse rate.

It is a further object of the present invention to combine in a device, the means for measuring ST segment deviation and pulse rate with signal processing means and memory means.

It is a further object of the present invention to provide a device for monitoring, analyzing, and storing information of pulse rate and ST segment deviation in a package that can be easily and unobtrusively attached to a patient for use, for example, during an exercise routine, or long term monitoring.

The above and other objects of the present invention are realized in a device and system for measuring, conditioning and analyzing a cardiac EKG waveform. The system employs electrodes placed proximate to the patient's heart. These electrodes sense the heart induced EKG waveform and provide a corresponding signal to a signal conditioning circuit. The signal conditioning circuit processes the input signal in a manner that accentuates the ST segment, and produces a square wave that is pulse width modulated by the ST segment. The pulse width modulated square wave is analyzed to determine if and to what extent the ST segment has deviated from a normal value. Outputs, such as alarms, are activated contingent on the extent of ST deviation and/or changes in pulse rate.

The present invention can be more fully understood from the following detailed description of a specific illustrative embodiment thereof, including drawings, of which:

Figure 4A:
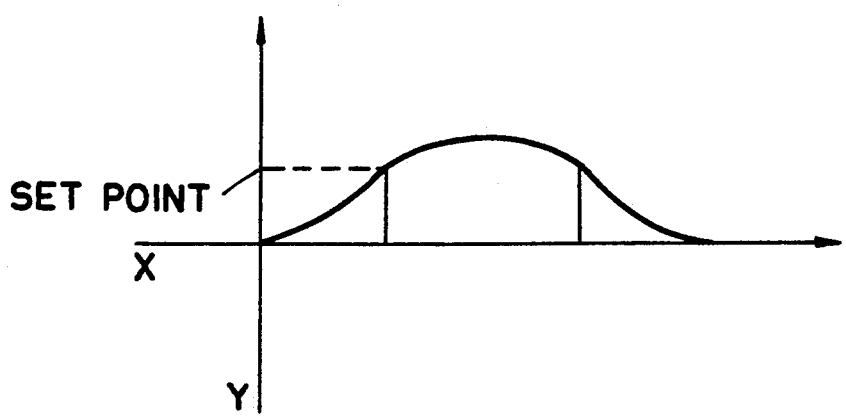

FIG. 4 provides three separate EKG waveforms showing the resulting signal blip associated with (a) normal ST segment, (b) depressed ST segment and (c) elevated ST segment.

Figure 5A:
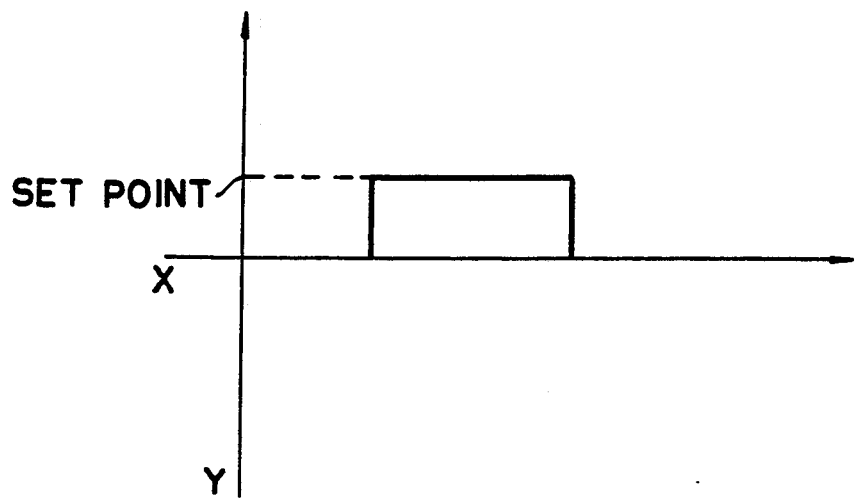
Figure 5B:
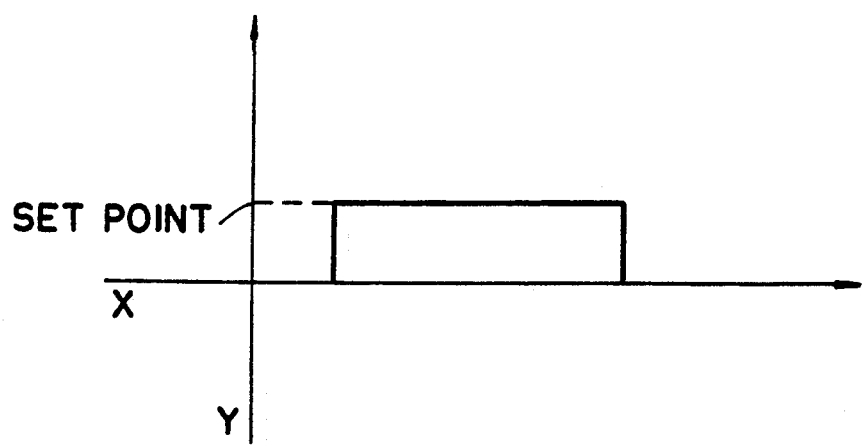
Figure 5C:
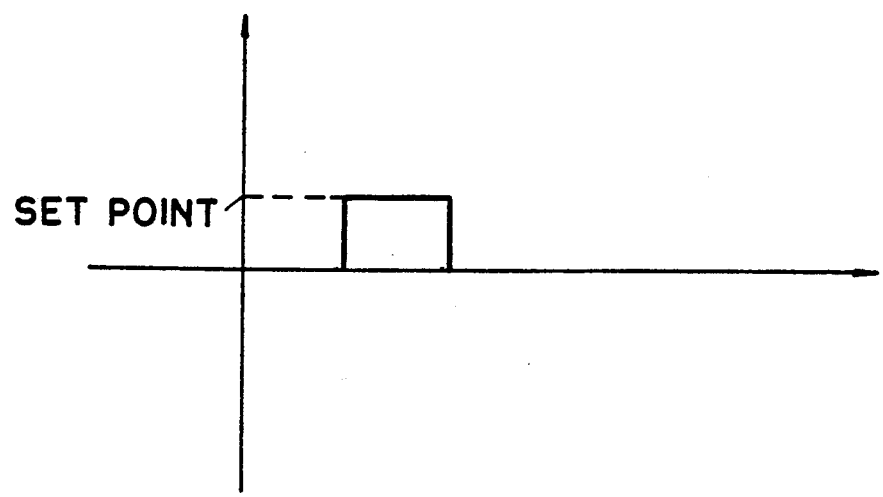

FIG. 5 provides three separate EKG waveform pulses showing (a) normal ST segment, (b) depressed ST segment and (c) elevated ST segment.

Figure 2:
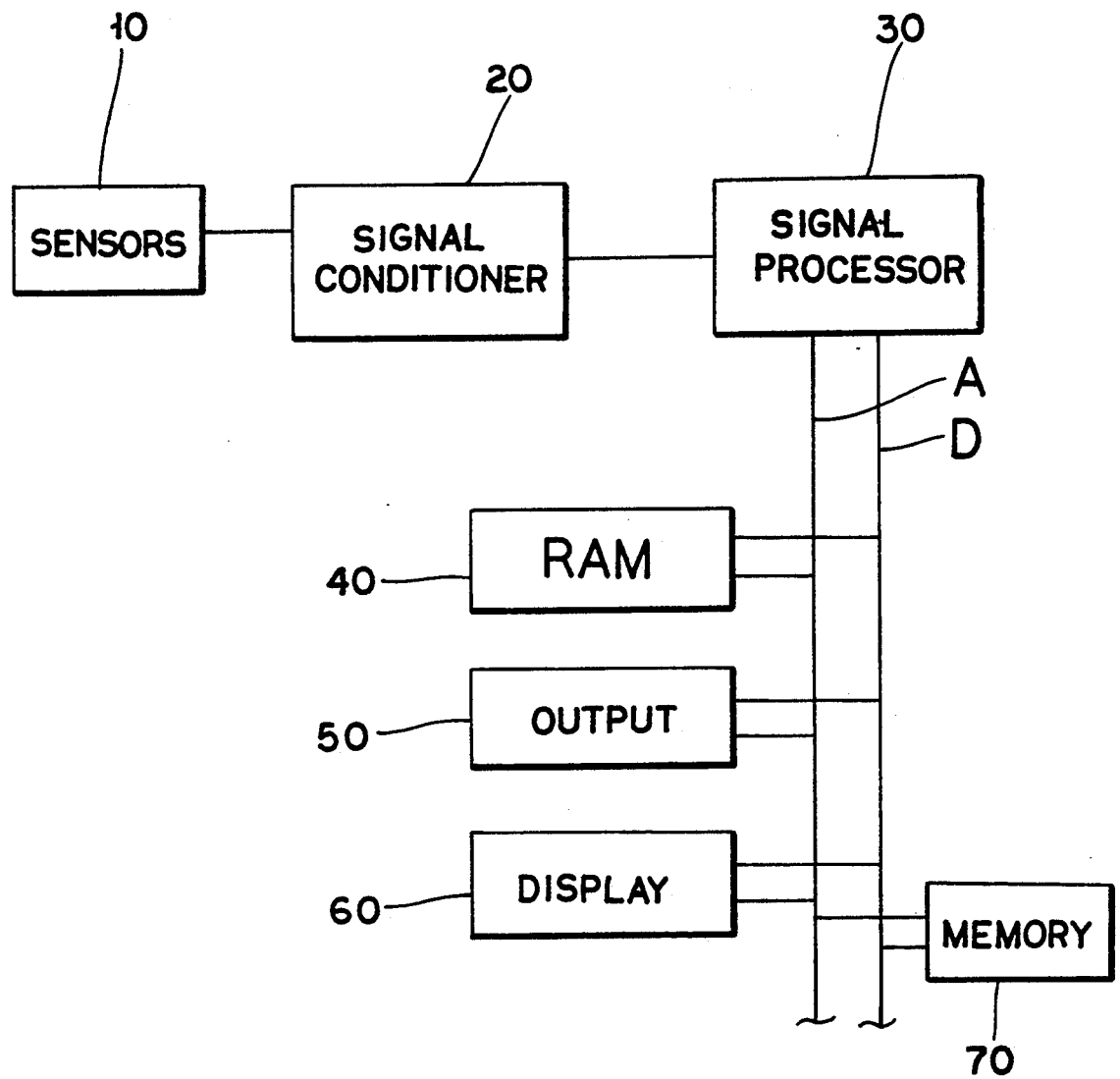
FIG. 2 is a block diagram of system components.

In FIG. 2, the system components are shown in block diagram form. Sensors, 10 incorporate plural electrodes placed onto the patient proximate to the heart. These sensors measure the EKG waveform providing an output signal corresponding to this waveform as an input to the signal conditioning unit, 20.

Figure 3:
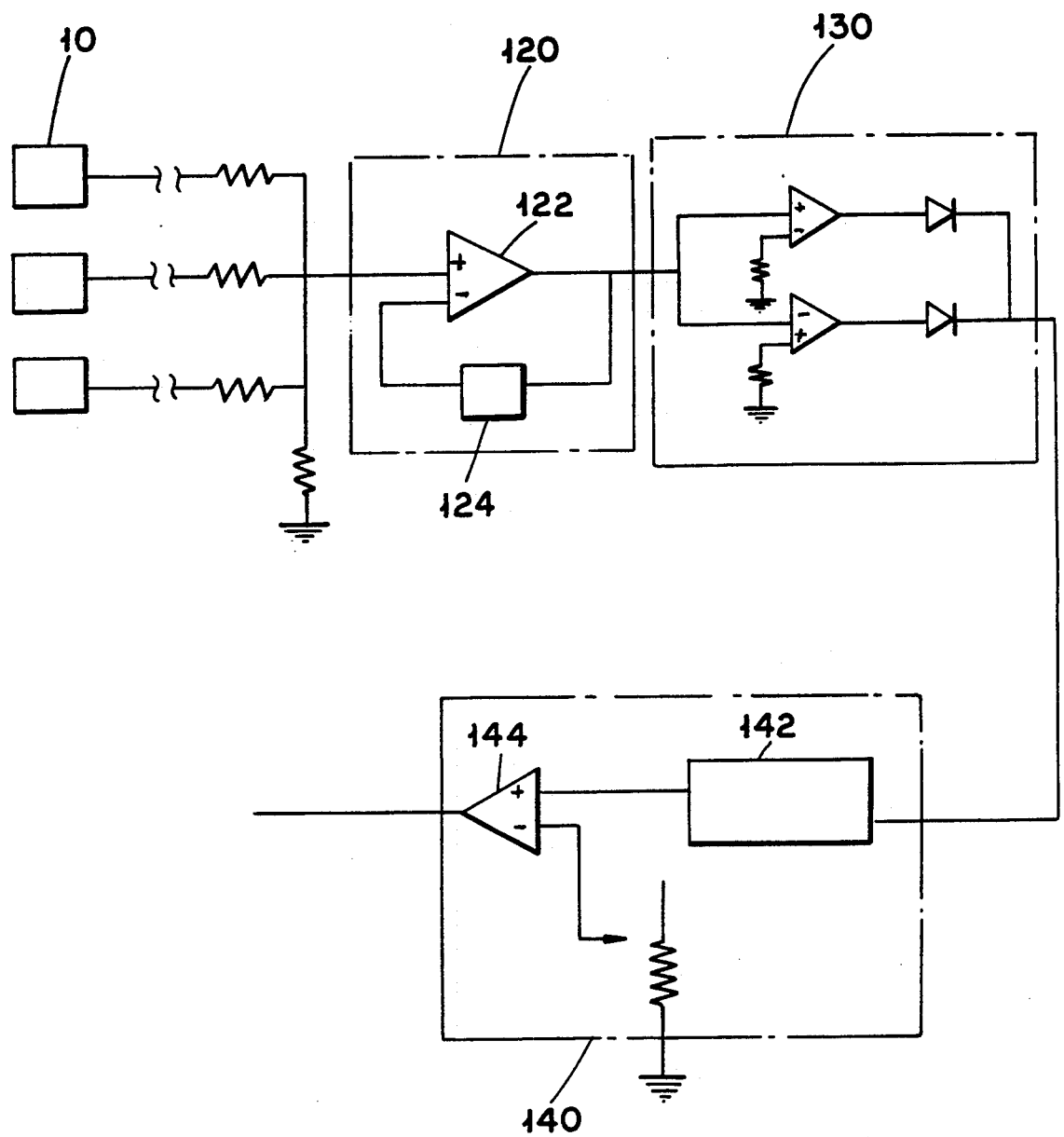
FIG. 3 is an electrical schematic of the signal conditioning circuit.

Signal conditioning unit 20 incorporates the electrical circuits shown schematically in FIG. 3. In FIG. 3, the output from the plural sensors form the combined input to the automatic again control (AGC) circuit 120. Circuit 120 comprises an amplifier 122 for increasing the received signal strength. This circuit also normalizes the signal via feedback loop 124 providing a uniform EKG in terms of voltage. In this manner, the AGC provides a scaled EKG waveform to Absolute Value (AV) circuit 130. AV circuit 130 employs two amplifiers, one inverting, one standard, each connected in series with a single diode and connected in parallel with respect to the output from the AGC. The AV circuit acts to convert the EKG alternating current signal into a direct current (DC) signal by inverting all negative portions of the EKG waveform.

Figure 1A:
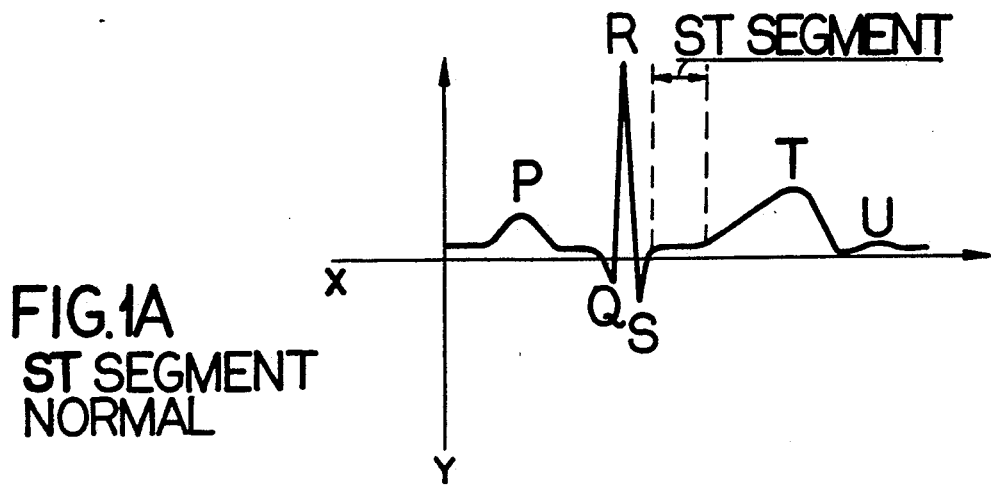
FIGS. 1A, 1B and 1C are showings of typical human EKG waveforms representing (a) normal ST segment (b) depressed ST segment and (c) elevated ST segment.
Figure 1B:
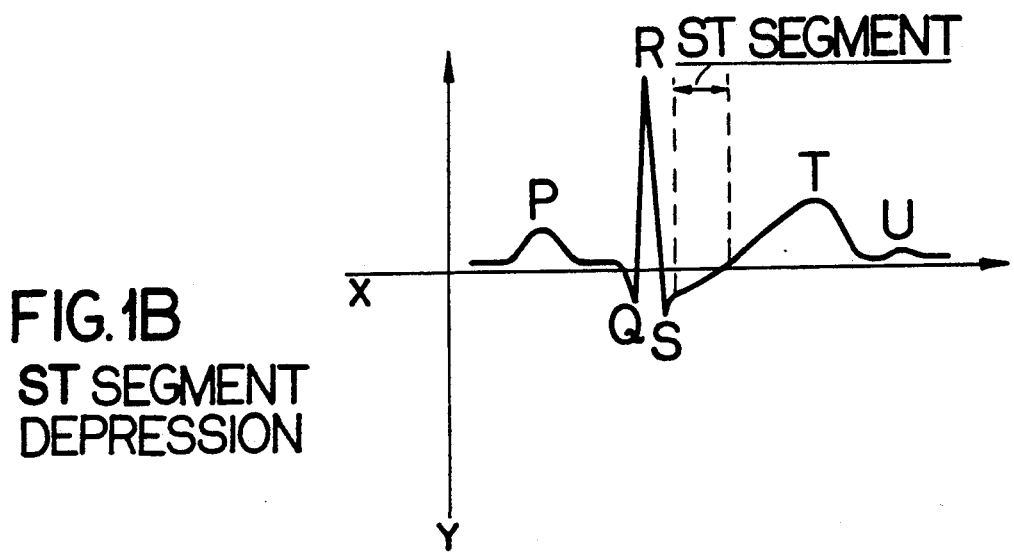
Figure 1C:
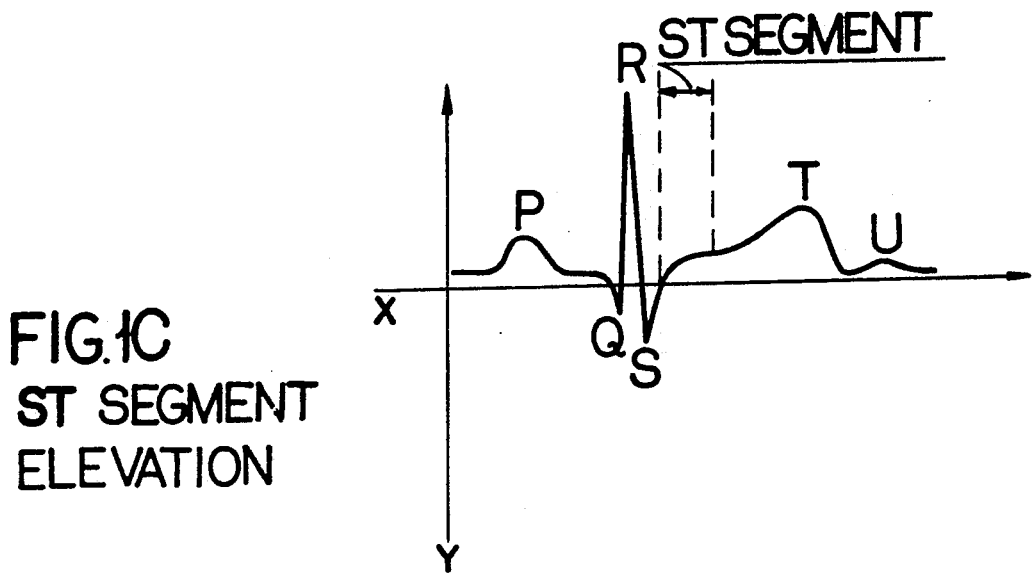

The DC output of the AV circuit 130 in FIG. 3 is fed into a pulse width modulation (PWM) circuit, 140. PWM comprises a low pass filter 142 in series with a gated pulse generating amplifier 144. The output of PWM 140 is a square wave at constant amplitude and a frequency equivalent to the heart beat, i.e., pulse rate. In this circuit, the low pass filter 142 acts to convert a heterogeneous EKG waveform into a series of blips, each corresponding to a heart beat and characterized by a single peak (point R in FIG. 1) followed by a gradual return to the isoelectric line. This blip is entered into the gated pulse generating amplifier 144 and compared to a user selected set point. In this context, the set point is a positive voltage value that is constantly compared to the incoming EKG signal. When the EKG signal amplitude exceeds this set point, the pulse generating amplifier starts a pulse at that amplitude in the form of a square wave. As the trailing edge of the EKG blip again passes through this set point. The pulse generating amplifier terminates the pulse.

The width of each pulse forming the square wave from PWM 140 is modulated by the location of the ST segment in the original EKG waveform. An elevated ST segment produces a shorter pulse width while a depressed ST segment produces a longer pulse width.

The ST segment deviation is, by definition, the deviation via elevation or depression of the ST segment from a known normal or control ST segment reading. In determining the ST segment deviation, the output of PWM 140 is fed to signal processor 30 (in FIG. 2). The ST segment deviation is the absolute value of the difference between the stored normal ST segment modulated pulse width and the current or real time ST segment modulated pulse width.

In operation, the system picks up and normalizes a patient's EKG. FIG. 4 provides three EKG waveforms corresponding to (a) normal ST segment, (b) depressed ST segment and (c) elevated ST segment, sampled from the above-described circuit after passing through the absolute value circuit and low pass filter. More particularly, each of the waveform shown in FIG. 4 depicts the intermediatory blip waveform and the impact on blip length made by the relative position of the ST segment in the EKG waveform. As can be seen, the negative portions of the high frequency component of the signal removed leaving the more gradually declining rounded blip. Although this process removes some information, it will be seen that the ST segment information is enchanced and made more accessible.

In FIG. 5, the square wave output from the gated square wave generator (144, in FIG. 3) is depicted for (a) normal ST segment, (b) depressed ST segment and (c) elevated ST segment. The produced pulses are initiated at an amplitude associated with a selected set point (as indicated for each of the waveforms in FIGS. 4 and 5). The pulses presented in FIG. 5 begin when the amplitude of the blip in FIG. 4 reaches and equals the set point provided to the square wave generator. Thereafter, the pulses shown in FIG. 5 continue at constant amplitude for a time determined by the length of the rounded blip. In this regard, as the signal drops back toward zero in the blip, it will pass through the set point value again; at the time that this occurs, the pulse is terminated creating a pulse width of a given magnitude.

A normal ST segment is routinely found close to the isoelectric line and, therefore, inverted by the absolute value circuit. An elevated St segment, due to its elevated location, upon inversion represents a small contribution to the total waveform and, therefore, produces a relatively short blip (see FIG. 4C). Upon further processing, this narrow blip produces a proportionally narrower pulse and as such indicative of ST segment elevation (see FIG. 5C).

Figure 4B:
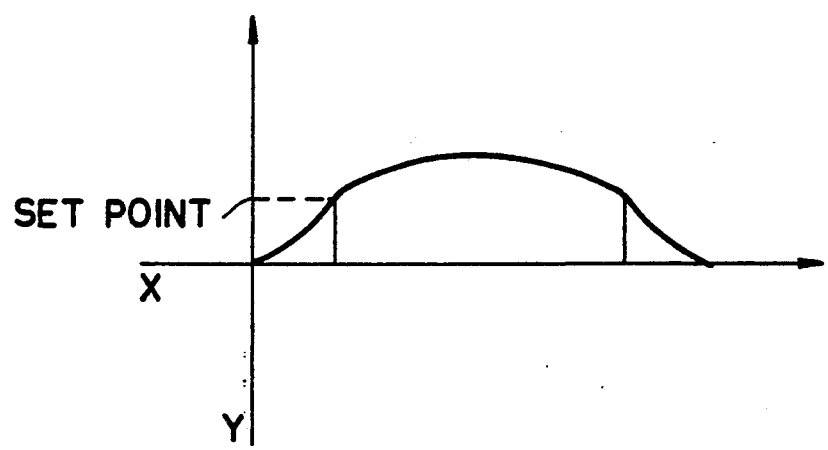
Figure 4C:
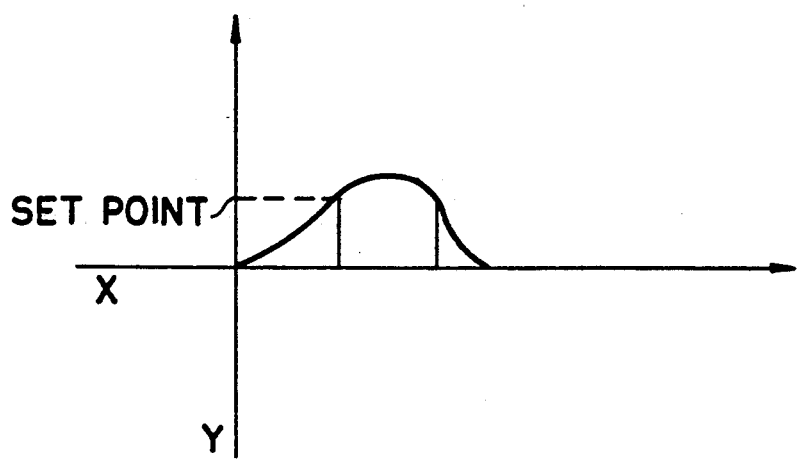

The depressed ST segment represents a relatively large negative value, and upon inversion, significantly expands the relative length of the blip (see FIG. 4B). This will result in the lengthening of the pulses as the set point is crossed for a second time after a much longer time interval (see FIG. 5B).

As discussed above, current ST segment deviation is simply determined by comparison between the current ST segment modulated pulse width and a stored normal pulse width. For illustrative purposes, this comparison is made digitally by microprocessor based central processing unit (CPU) as integrated with memory, output, and display devices. For example, in FIG. 2, CPU 30 reads the incoming pulse width modulated signal from signal conditioner 20, samples the incoming signal pursuant to a signal averaging algorithm, storing portions of information in RAM 40, or bulk memory 70. Display 60 in the form of e.g., liquid crystal display (LCD) provides the user current information, while output 50 includes alarms on ST deviation excursions.

A microcompressor based system provides the most flexibility as the incoming signal can be manipulated in a variety of ways. Greater overall accuracy can be developed by taking time averaged values of the pulse widths and using numerical techniques to remove artifacts, noise or other sources of errors.

The use of system memory permits an extended analysis of ST segment excursions and patterns thereof occurring over, for example, a stressful 24 hour period. In addition, the microprocessor system permits the exchange of system control algorithms, the adjustment of set point values, alarm values, and pre-set normal pulse widths. Also, the system algorithms may determine a "normal" pulse width by operating a learn cycle, measuring the EKG during a known non-stressful period as defined by the user, and storing a time-averaged value of the "normal" pulse width for later use in calculating ST segment deviation.

Alternatively, signal processor 30 can include discrete electronics for analog processing of the pulse width modulated square wave, extract the ST segment deviation in real time, and control output alarm accordingly, without the need for digital processing.

The above described arrangement is merely illustrative of the principles of the present invention. Numerous modifications and adaptations thereof will be readily apparent to those skilled in the art without departing from the spirit and scope of the present invention.

What is claimed is:

1. An apparatus for monitoring and converting an EKG waveform comprising electrical sensors for detecting said EKG waveform, a signal conditioning means in communication with said electrical sensors for inverting all negative portions of said detected EKG waveform, a pulse generator means including a low pass filter means for generating pulses having pulse width modulated by a change in location of a ST segment of said EKG waveform, and a comparator means for determining the amount of ST segment deviation from a normal value.

2. In an apparatus as in claim 1, further comprising output means including an alarm for indicating if said ST segment deviation has exceeded pre-selected limits.

3. In a system for monitoring a heart for the detection of abnormalities is an EKG signal apparatus comprising:
   (a) signal acquisition means for detecting signal;
   (b) signal conditioning means in communication with said signal acquisition means and comprising: means for receiving said detected EKG signal; signal adjustment means for normalizing said detected EKG signal; and a signal inverting means for converting said normalized EKG signal into a DC signal; and
   (c) pulse modulating means in communication with said signal conditioning means and comprising: means for receiving said DC signal; low pass filter means for processing said DC signal; and pulse generating means generating an output pulse, wherein said output pulse is pulse width modulated by said processed DC signal.

4. The apparatus of claim 3, wherein said signal adjustment means further comprises an automatic gain control circuit with feedback control of said detected EKG signal.

5. The apparatus of claim 4, wherein said signal inverting means further comprises an inverting amplifier in parallel with a standard amplifier, wherein each amplifier is in series with a separate diode.

6. The apparatus of claim 5, wherein said pulse generating means comprises a gated pulse generating amplifier.

7. The apparatus of claim 6, wherein said gated pulse generating amplifier is adapted to receive a set point value, and compare said received C signal to said point value.

8. The apparatus of claim 7, wherein said gated pulse generating amplifier generates a pulse when said DC signal exceeds said set point value, and terminates said pulse when said DC signal drops below said set point value.

9. The apparatus of claim 8, wherein said gated pulse generating amplifier generates a square wave.

10. A method for detecting ST segment deviation comprising the steps of:
    a) detecting an EKG waveform;
    b) conditioning the EKG waveform by inverting all negative portions of said waveform to positive values and passing said inverted EKG waveform through a low pass filter;
    c) generating a pulse wherein said pulse is modulated by the change in ST segment location of said EKG waveform; and
    d) comparing said generated puls with a pulse modulated by an EKG waveform having a normal ST segment location.

11. The method of claim 10, wherein said conditioning the EKG waveform includes normalizing the gain in said EKG waveform.

12. The method of claim 10 further comprising the step of collecting plural pulses and determining an ST deviation based on time averaged changes in the pulses as generated.

* * * * *